(12) United States Patent
Sun

(10) Patent No.: US 6,241,783 B1
(45) Date of Patent: Jun. 5, 2001

(54) FORMALDEHYDE SCAVENGING IN MICROBIOCIDAL ARTICLES

(75) Inventor: Gang Sun, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/416,203

(22) Filed: Oct. 8, 1999

Related U.S. Application Data

(60) Continuation-in-part of application No. 09/102,525, filed on Jun. 22, 1998, now Pat. No. 6,077,319, which is a division of application No. 08/713,406, filed on Sep. 13, 1996, now Pat. No. 5,882,357.

(51) Int. Cl.[7] .................. D06M 11/07; D06M 13/148; D06M 13/352; D06M 13/358
(52) U.S. Cl. .................. 8/189; 8/115.51; 8/115.7; 8/190; 8/115.58; 8/115.59; 8/115.69
(58) Field of Search .................. 8/108.1, 189, 115.69, 8/115.51, 115.7, 190, 115.58, 115.59; 510/302, 319, 383; 252/8.86, 8.84; 424/404, 405

(56) References Cited

U.S. PATENT DOCUMENTS

| | | | |
|---|---|---|---|
| 2,950,553 | 8/1960 | Hurwitz | 8/183 |
| 3,061,469 | 10/1962 | Manowitz et al. | 8/189 |
| 3,260,565 | 7/1966 | Beachem | 8/116.3 |
| 3,401,005 | 9/1968 | Katz | 8/189 |
| 3,445,279 | 5/1969 | Abrahams et al. | 117/143 |
| 3,488,701 | 1/1970 | Herbes et al. | 8/189 |
| 3,565,824 | 2/1971 | Pierce, Jr. et al. | 252/429 |
| 3,576,591 | 4/1971 | Cusano | 8/185 |

(List continued on next page.)

FOREIGN PATENT DOCUMENTS

| | | |
|---|---|---|
| 2500430 | 7/1975 | (DE) . |
| 4125431 | 7/1992 | (DE) . |
| 2161399 | 1/1986 | (GB) . |

OTHER PUBLICATIONS

*Chemical Abstracts*, 78(12), p. 66, col. 1, No. 73517u, Mar. 26, 1973.
Gagliardi, et al., "Antibacterial finishes," *American Dyestuff Reporter*, 2:31–40, Jan. 1962.
Rigby, et al., "Medical textiles—Textile materials in medicine and surgery," *Textile Horizons*, pp. 42–45 (1993) (month unknown/unavailable).
Sun, et al., "A new cyclic n-halamine biocidal polymer," *Ind. Eng. Chem. Res.*, 33:168–170 (1994) (month unknown/unavailable).
Vigo, "Antimicrobial fibers and polymers," *Manmade Fibers: Their Origin and Development*, pp. 214–226 (1992) (month unknown/unavailable).
Vigo, "Advances in microbial polymers and materials," *Biotechnology and Bioactive Polymers*, Edited by Gebelein and Carraher, Plenum Press, New York, pp. 225–237 (1994) (month unknown/unavailable).
Worley, et al., "Biocidal polymers," *Trends in Polymer Science*, 4(11):364–370 (1996) (month unknown/unavailable).

Primary Examiner—Caroline D. Liott
(74) Attorney, Agent, or Firm—Townsend & Townsend & Crew LLP

(57) ABSTRACT

Improved methods for durable and regenerable antimicrobial finishing of fabrics are disclosed. In certain embodiments, the methods reduce the amount of free-formaldehyde released during processing by using a formaldehyde scavenger such as a polyol. The improved process imparts regenerable antimicrobial functions to cellulose articles including textiles, papers, wood pulp, and any cellulose-containing materials. The treated product acquire antimicrobial properties after being treated with a halogenated solution.

33 Claims, 3 Drawing Sheets

U.S. PATENT DOCUMENTS

| | | | |
|---|---|---|---|
| 3,594,113 | 7/1971 | Lifland et al. | 8/115.6 |
| 3,650,667 | 3/1972 | Luechauer | 8/111 |
| 3,674,811 | 7/1972 | Kern | 8/189 |
| 3,812,201 | 5/1974 | Bey | 525/418 |
| 4,199,322 | 4/1980 | Danna et al. | 8/186 |
| 4,284,758 | 8/1981 | North | 528/245 |
| 4,300,898 | 11/1981 | North | 8/185 |
| 4,306,872 | 12/1981 | Herbes et al. | 8/189 |
| 4,396,391 | 8/1983 | North | 8/181 |
| 4,585,650 | 4/1986 | Newberry, Jr. et al. | 424/73 |
| 4,844,891 | 7/1989 | Rosen et al. | 424/76.4 |
| 5,104,649 | 4/1992 | Jansson et al. | 424/78.31 |
| 5,208,016 | 5/1993 | Ohmae et al. | 424/78.27 |
| 5,221,574 | 6/1993 | Branch et al. | 428/289 |
| 5,352,693 | 10/1994 | Farina | 514/398 |
| 5,405,862 | 4/1995 | Farina et al. | 514/389 |
| 5,490,983 | 2/1996 | Worley et al. | 424/405 |
| 5,610,189 | 3/1997 | Whiteley | 514/557 |
| 5,707,404 | 1/1998 | Andrews et al. | 8/189 |

5,5-Dimethylhydantoin 2,2,5,5-Tetramethyl-
4-imidazolidinone 4,4,5,5-Tetramethyl-
2-imidazolidinone Triazine-1,3,5-trione Monomethoxymethyl-
5,5-dimethylhydantoin 1,3-Dimethoxymethyl-
5,5-dimethylhydantoin

FORMALDEHYDE SCAVENGING IN MICROBIOCIDAL ARTICLES

CROSS-REFERENCES TO RELATED APPLICATIONS

This application is a continuation-in-part of U.S. patent application Ser. No. 09/102,525, filed Jun. 22, 1998, now U.S. Pat. No. 6,077,319, which is a divisional of U.S. patent application Ser. No. 08/713,406, filed Sep. 13, 1996, now U.S. Pat. No. 5,882,357, both disclosures of which are hereby incorporated by reference in their entirety for all purposes.

FIELD OF THE INVENTION

In general, this invention relates to methods for generating biocidal materials and improved methods for producing them. In particular, this invention provides improved processes for producing biocidal materials in the absence of toxic materials.

BACKGROUND OF THE INVENTION

Studies indicate that formaldehyde is a potential human carcinogen. Airborne concentrations above 0.1 ppm can cause irritation of the eyes, nose and throat. The severity of irritation increases as concentrations increase; at 100 ppm it is immediately dangerous to life and health. Facilities that manufacture, consume or produce formaldehyde must control workers exposure in accordance with strict regulations. Dermal contact causes various skin reactions including sensitization, which could force persons thus sensitized to find other work.

The permissible exposure limit (PEL) for formaldehyde in all workplaces (including general industry, construction, and maritime, but not in agriculture) covered by the Occupational Safety and Health Act is 0.75 ppm measured as an 8-hour time weighted average (TWA). This standard includes a 2 ppm short-term exposure limit (STEL) (ie., maximum exposure allowed during a 15-minute period). The "action level" is 0.5 ppm measured over 8 hours.

U.S. Pat. No. 5,882,357, which issued to Sun et al., on Mar. 16, 1999, discloses the use of heterocyclic amines such as 1,3-dimethylol-5,5-dimethylhydantoin (DMDMH) and monomethylol-5,5-dimethylhydantoin (MDMH), to impart durable and regenerable antimicrobial functions to inter alia, cellulose materials. In certain instances, during the process of imparting antimicrobial properties to cellulosic materials, free-formaldehyde can be generated. Moreover, when these microbiocidal textiles are stored under humid conditions, free-formaldehyde can be released.

Thus, despite the advances made by U.S. Pat. No. 5,882, 357, there remains a need to reduce the amount of formaldehyde released during preparation of microbiocidal products. The present invention remedies such need by providing processes that reduce the amount of formaldehyde during the preparation of microbiocidal articles.

SUMMARY OF THE INVENTION

Formaldehyde causes eye, upper respiratory tract and skin irritation and is a skin sensitizer. Sensory irritation occurs at concentrations as low as 0.1 ppm and significant irritation of the nose and throat occurs at concentration of about 1 ppm. Moreover, dermal contact causes various skin reactions, thus forcing persons sensitized to find other work. In certain instances, a byproduct of producing antimicrobial articles is the presence of free-formaldehyde. To remedy this drawback, the present invention provides a process for preparing a microbiocidal article with a reduction in free-formaldehyde release, the process comprising: (a) immersing the article in an aqueous treating solution which comprises a heterocyclic amine and a polyol; and (b) treating the article with a halogenated solution, thereby rendering the article microbiocidal with a reduction in free-formaldehyde release. Preferably, the aqueous treating solution further comprises a catalyst and a wetting agent.

In certain preferred aspects, formaldehyde is scavenged by a polyol that reduces the formaldehyde to a harmless product. The preferred polyols include, but are not limited to, diethylene glycol or ethylene glycol. In certain preferred embodiments, the heterocyclic amine is alkylated or partially alkylated. Suitable heterocyclic amines for use in the present invention include, but are not limited to, DMDMH, alkylated DMDMI, or a mixture of DMDMH and its unmethylolated dimethylhydantoin (DMH) derivative. Using the aforementioned heterocyclic amines, it is possible to produce microbiocidal articles with low potential for formaldehyde release.

In another aspect, the present invention provides a process for preparing a microbiocidal article with a reduction in free-formaldehyde release, the process comprising: (a) immersing the article in an aqueous treating solution which comprises an alkylated heterocyclic amine; and (b) treating the article with a halogenated solution, hereby rendering the article microbiocidal with a reduction in free-formaldehyde release. In this aspect, the alkylated or partially alkylated heterocyclic amine is less amenable to releasing formaldehyde than a heterocyclic amine. Optionally, a polyol is used in conjunction with an alkylated heterocyclic amine to reduce formaldehyde. Moreover, a catalyst and a wetting agent can optionally be used in the aqueous treating solution.

These and other aspects of the present invention will be readily apparent when read with the detailed description and figures that follow.

DEFINITIONS

As used herein, the acronym "DMDMIH" refers to 1,3-dimethylol-5,5-dimethylhydantoin.

As used herein, the acronym "MDMH" refers to monomethylol-5,5-dimethylhydantoin.

As used herein, the acronym "DMDHEU" refers to dimethyloldihydroxy-ethylene urea.

As used herein, the acronym "DMH" refers to dimethyloldihydroxy-ethylene urea.

The term "alkylated" or "partially alkylated" refers to adding alkyl functional groups containing about 1 to 6 carbon atoms to heterocyclic amines having a free hydroxy group (e.g., hemiacetal functionality). These alkyl groups include, but are not limited to, methyl, ethyl, propyl, isopropyl, butyl, n-pentyl and the like. Partially alkylated means adding alkyl functional groups, but still leaving at least one free hydroxy group (e.g., hemiacetal functionality). In preferred embodiments, DMDMH and MDMH are alkylated or partially alkylated.

DETAILED DESCRIPTION OF THE INVENTION AND PREFERRED EMBODIMENTS

Figure 1:
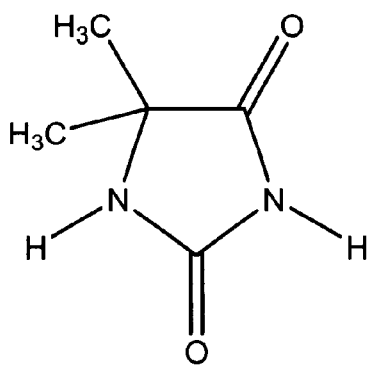
FIG. 1 illustrates various heterocyclic amines suitable for use in the present invention.
Figure 1:
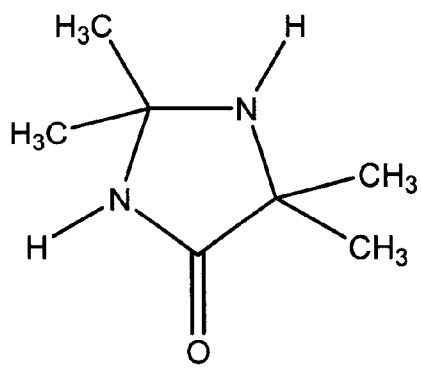
Figure 1:
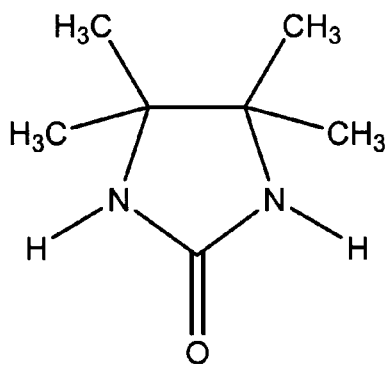
Figure 1:
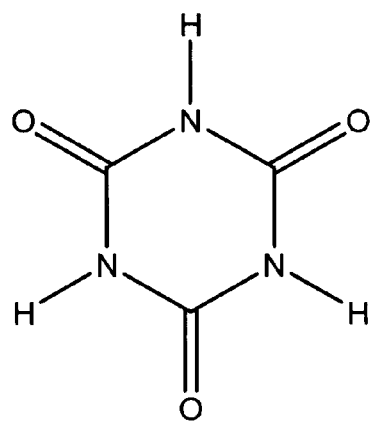
Figure 1:
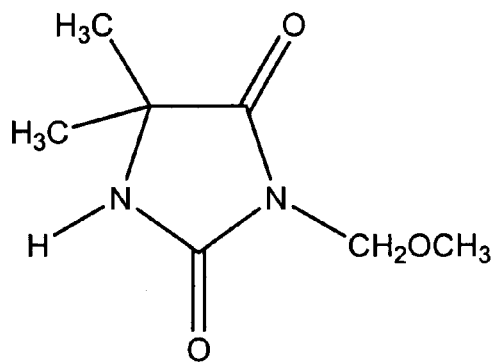
Figure 1:
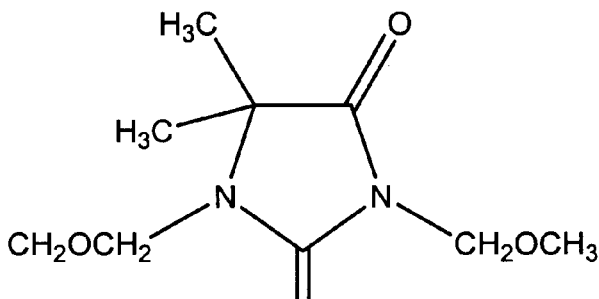

Heterocyclic amines have been used as agents to impart durable and regenerable antimicrobial functions to cellulose materials. In certain instances, a by-product of producing antimicrobial articles is the presence of free-formaldehyde. As explained above, the presence of free-formaldehyde is undesirable for health and safety reasons.

As such, the present invention provides a process for preparing a microbiocidal article with a reduction in free-formaldehyde, the process comprising: (a) immersing the article in an aqueous treating solution which comprises a heterocyclic amine and a polyol; and (b) treating the article with a halogenated solution, thereby rendering the article microbiocidal with a reduction in free-formaldehyde. Preferably, the aqueous treating solution further comprises a catalyst and a wetting agent.

A wide variety of articles are suitable for use in the present invention. These articles include, but are not limited to, textiles such as cellulosic fabric, cellulosic yarn, and cellulosic fiber, wherein the foregoing can be woven or nonwoven; polymers such as polyester and cellulose; cotton fabric/polyester blends; polyester/rayon blends, wood materials such as wood pulp, paper, cardboard; garments such as shirts, pants, undergarments, coats, hoods, cloaks, hats, gloves, protective garments, surgical gowns, garments, masks, boots, aprons, and hospital and laboratory supplies. Those of skill in the art will know of other articles suitable for use in the processes of the present invention.

Using the methods of the present invention, the articles, such as textiles, provide microbiocidal protection with a concomitant decrease or elimination of formaldehyde production. The article (e.g., a fabric) is immersed in an aqueous treating solution. In certain embodiments, the aqueous treating solution comprises a heterocyclic amine and a polyol. Preferably, the treating solution also comprises a wetting agent and a catalyst. As used herein, "wetting agent" refers to a substance that increases the rate at which a liquid spreads across a surface, i.e., it renders a surface nonrepellent to a liquid. Examples of suitable wetting agents include, but are not limited to, TRITON® X-100 which is generically a polyoxyethylene (10) isooctylphenyl ether commercially available from Sigma Chemical Co., St. Louis, Mo; SEQUAWET® which is generically, a wetting agent containing nonionic surfactants commercially available from Sequa Chemical Inc., Chester, S.C.; and AMWET® which is generically, a wetting agent containing nonionic surfactants commercially available from American Emulsions Co., Dalton, Ga. Other wetting agents suitable for use in the present invention will be known to and used by those of skill in the art. As used herein, "catalyst" refers to a substance that augments the rate of a chemical reaction without itself being consumed. Suitable catalysts for use in the present invention include, but are not limited to, magnesium salts, zinc salts and ammonium salts. In presently preferred embodiments, the catalysts include, but are not limited to, Catalyst 531, $MgCl_2$, $Mg(NO_3)_2$, $Zn(NO_3)_2$ and $NH_4NO_3$.

After the article, such as a fabric, is immersed in the above-described aqueous treating solution, the article is then treated with a halogenated solution, such as a halogenated aqueous solution. The halogenated solution can be a chlorine solution, a bromine solution, and combinations thereof, etc. In a presently preferred embodiment, the halogenated solution is sodium hypochlorite (e.g., a chlorine bleach solution such as CLOROX®). The treatment of the article with a halogenated solution renders the article microbiocidal.

Figure 2:
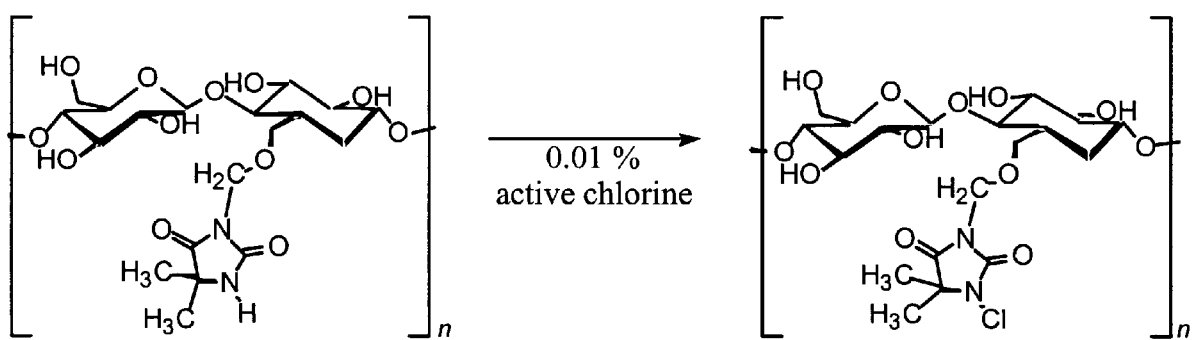
FIG. 2 illustrates a mechanism of imparting microbiocidal properties using a method of the present invention.

As disclosed in U.S. Pat. No. 5,882,357, the articles become microbiocidal by grafting a heterocyclic N-halamine structure on the article. With reference to FIG. 2, incorporation of a halamine on a fabric such as cotton, with subsequent halogenation renders the article microbiocidal. However, in certain embodiments, in the process of producing such microbiocidal articles, free-formaldehyde can be produced. Moreover, when microbiocidal articles are stored under humid conditions, free-formaldehyde can be generated. As discussed above, formaldehyde can cause sever skin reactions and is quite toxic to humans. Thus, from an industrial hygiene point of view, formaldehyde reduction or elimination is advantageous.

Figure 3:
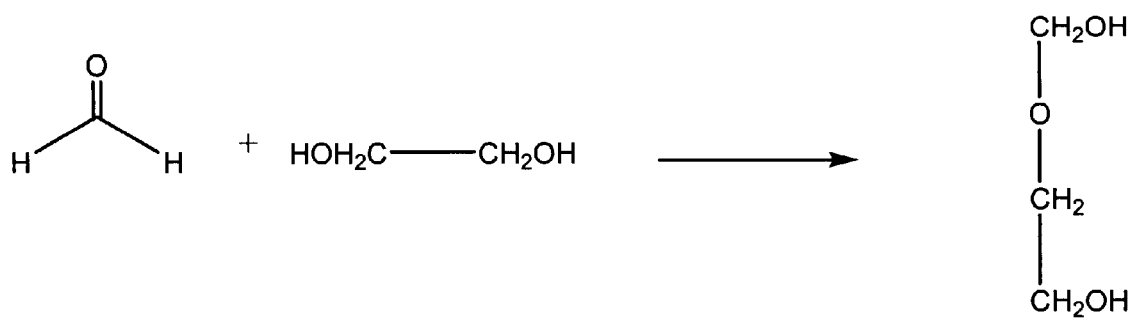
FIG. 3 illustrates a mechanism for formaldehyde scavenging using a process of the present invention.

Surprisingly, the inventor has discovered that if a polyol is used in the process of making the article microbiocidal, free-formaldehyde can be reduced or eliminated entirely. Without being bound by any particular theory, it is believed that the formaldehyde reacts with a polyol and is reduce to a harmless product. With reference to FIG. 3, one possible mechanism of action of scavenging formaldehyde is shown. The term "polyol" refers to a compound containing a plurality of hydroxyl groups. Suitable examples include, but are not limited to, ethylene glycol, propylene glycol, diethylene glycol, 1,2-propylene glycol, 1,3-propylene glycol, 1,2-butylene glycol, 1,3-butylene glycol, 1,4-butylene glycol, polyethylene glycols having the formula $HO(CH_2CH_2O)_nH$ wherein n is about 1 to about 50, glycerin, and the like, and combinations thereof. The preferred polyols are diethylene glycol and ethylene glycol.

In certain embodiments, the heterocyclic amine: polyol ratio used in the processes of the present invention is generally between about 0.2–1.0:1.0–6.0. Preferably, the heterocyclic amine: polyol ratio is between about 0.5–1.0:1.0–3.0. In certain preferred embodiments, the ratio is between about 0.5–1.0:1.0–3.0 for DMDMH: polyol and between about 0.5–1.0:1.0–2.0 for MDMH: polyol. The foregoing ratios are based on a mole/mole ratio. Microbiocidal fabrics treated using polyols in the aqueous treating solution achieved significant formaldehyde reduction on cotton and on polyester/cotton blends.

In certain aspects of the present invention, several steps can optionally be inserted between steps (a) and (b) above. For instance, in certain preferred aspects, the method further comprises removing excess aqueous treating solution from the article before treating the article with a halogenated aqueous solution. In this aspect, the excess aqueous treating solution is removed by ordinary mechanical methods, such as by passing the article (e.g., textile) between squeeze rolls, by centrifugation, by draining or by padding. In a preferred embodiment, the excess aqueous treating solution is removed by padding.

In addition, the process optionally further comprises drying the article after removing excess aqueous treating solution to produce a dried article. In this aspect, the article is dried at a temperature ranging from about 50° C. to about 90° C. and, more preferably, at a temperature ranging from about 75° C. to about 85° C. for a period of time ranging from about 3 to about 8 minutes and, more preferably, for about 5 minutes.

Moreover, the dried article can optionally be cured to produce a cured article. The curing process is conducted at a temperature ranging from about 120° C. to about 200° C. and, more preferably, at a temperature ranging from about 140° C. to about 160° C. for a period of time ranging from about 3 to about 8 minutes and, more preferably, for about 5 minutes. The heating can be carried out in an oven, preferably one having a forced draft of air directed at the surface of the article and exhausting through a vent to remove fumes.

The cured article is then optionally washed to remove excess reagents. Washing of the treated article can be done with water. The covalent bonds formed are stable, insoluble, and durable to the mechanical agitation, spraying and rubbing that occurs in washing machines or in large scale continuous or batchwise textile washing equipment. In certain preferred embodiments, the process further comprises drying the washed article to remove water.

The article can optionally be dried before treating the article with a halogenated aqueous solution, to render the article microbiocidal. Drying of the article, such as a fabric, can be carried out by any ordinary means such as oven drying, line drying or, tumble drying in a mechanical clothes dryer. A drying temperature of about 80° C. to about 120° C. is particularly preferred. Suitable drying times are generally less than 15 minutes in duration.

In certain preferred aspects, the present invention provides a process for preparing a microbiocidal article with a reduction in free-formaldehyde release, comprising: (a) immersing the article in an aqueous treating solution which comprises a catalyst, a wetting agent, a heterocyclic amine and a polyol; (b) removing the excess treating solution from the article; (c) drying the article; (d) curing the article; (e) washing the cured article to remove excess reagents; (f) drying the washed article to remove water; and (g) treating the article with a halogenated aqueous solution, thereby rendering the article microbiocidal.

As used herein, "heterocyclic amine," refers to a 4- to 7-membered ring, having at least 3 members of the ring being carbon, and from 1 to 3 members of the ring being nitrogen, and from 0 to 1 member of the ring being an oxygen, wherein from 0 to 2 carbon members comprise a carbonyl group, and wherein at least 1 to 3 nitrogen atoms are substituted with a hydrogen or hydroxyalkyl group, such as —CH$_2$OH, or a alkoxyalkyl group, such as —CH$_2$OCH$_3$. After halogenation, at least one ring nitrogen has bonded thereto a halogen atom. In addition, the ring members can be further substituted with alkyl groups, such as methyl, ethyl, etc., or hydroxy groups. Heterocyclic N-halamines are generally disclosed in U.S. Pat. No. 5,490,983 issued to Worley, et al. on Feb. 13, 1996, the teachings of which are incorporated herein by reference for all purposes.

The preferred heterocyclic amines suitable for use in the present invention include, but are not limited to, monomethylol-5,5-dimethylhydantoin (MDMH), 1,3-dimethylol-5,5-dimethylhydantoin (DMDMH); monoalkylolated and dialkylolated derivatives of 2,2,5, 5-tetramethyl-1,3-imidazolidin-4-one, 6,6-dimethyl- 1,3,5-triazine-2,4-dione, 4,4,5,5-tetramethyl-1,3-imidazolidin-2-one, cyanuric acid and 5,5-dimethylhydantoin; and monoalkylated and dialkylated derivatives of monoalkylolated and dialkylolated derivatives of 2,2,5,5-tetramethyl-1,3-imidazolidin-4-one, 6,6-dimethyl-1,3,5-triazine-2,4dione, 4,4,5,5-tetramethyl- 1,3-imidazolidin-2-one, cyanuric acid, 5,5-dimethylhydantoin, 2,2,5,5-tetramethyl-1,3-imidazolidin-4-one and mixtures thereof Preferably the heterocyclic amine is monomethylol-5,5-dimethylhydantoin (MDMH), and 1,3-dimethylol-5,5-dimethylhydantoin (DMDMH) (see, FIG. 1). In certain preferred embodiments, the heterocyclic amine is DMDMH, an alkylated DMDMH, or a mixture of DMDMH and its unmethylolated dimethylhydantoin (DMH) or DMDHEU.

In certain other embodiments, the heterocyclic amine is alkylated. In general, the alkylation process involves reacting a hydantoin derivative (e.g., DMDMH or MDMH) and an alcohol in an alcoholic solution. Suitable alcohols include, but are not limited to, alkanols such as methanol, ethanol, propanol, butanol, and combinations thereof, etc. The reaction can be carried-out within the temperature range of between about 10° C. to about 100° C., and preferably within the range between of about 40° C. to 80° C. The duration of the reaction is about 1 to about 24 hours, and preferably for about 2 to about 6 hours. The pH of the reaction mixture can range between about 1.0 to about 6.0 and preferably within the range of between about 2.0 to about 4.0. The pH of the reaction solution can be adjusted with any suitable mineral acids including, but not limited to, sulfuric acid, nitric acid, phosphoric acid, hydrochloric acid; as well as any organic acid including, but not limited to, acetic acid, glycolic acid, maleic acid, lactic acid, tartaric acid, oxalic acid, citric acid or combinations thereof.

In another embodiment, the aqueous treating solution comprises an alkylated heterocyclic amine or partially alkylated heterocyclic amine and a polyol. Preferably, the alkylated or partially alkylated heterocyclic amine: polyol ratio is generally as set forth above. Using both an alkylated or partially alkylated heterocyclic amine and a polyol has an additive effect on the reduction on formaldehyde. For example, by admixing alkylated DMDMH with diethylene glycol the formaldehyde release reduction reached about 50–85% on cotton and about 55%–80% on polyester/cotton blends.

In yet another embodiment, the aqueous treating solution of the present invention comprises a heterocyclic amine (e.g. DMDMH or MDMH), an alkylated heterocyclic amine (e.g., alkylated or partially alkylated DMDMH or MDHM) and a polyol such as diethylene glycol. In certain embodiments, the heterocyclic amine (i.e., the combination of heterocyclic amine and alkylated heterocyclic amine or partially alkylated): polyol ratio used in the processes of the present invention is generally between about 0.2–1.0:1.0–6.0 mole/mole. Preferably, the heterocyclic amine (i.e., the combination of heterocyclic amine and alkylated heterocyclic amine or partially alkylated): polyol ratio is between about 0.5–1.0:1.0–3.0 mole/mole. By admixing a heterocyclic amine, an alkylated heterocyclic amine (or partially alkylated heterocyclic amine) and a polyol, formaldehyde release was reduced in a range of about 70% on cotton and about 80% on polyester/cotton blends.

In another embodiment, the aqueous treating solution for imparting low formaldehyde and formaldehyde free antimicrobial finishing comprises a heterocyclic amine (e.g., DMDMH, alkylated DMDMH, or a mixture thereof) with DMDHEU. In a preferred embodiment, the foregoing aqueous treating solution optionally comprises a polyol. In certain embodiments, the heterocyclic amine : DMDHBEU ratio is generally between about 0.2–1.0:1.0–6.0 and preferably between about 0.5–1.0: 1.0–0.5 mole/mole. In certain embodiments, the heterocyclic amine: polyol ratio is between about 0.2–1.0: 1.0–6.0, and preferably, between about 0.5–1.0:1.0–3.0 mole/mole. Admixing DMDMH or MDMH with DMDHEU results in formaldehyde reduction in a range of about 70% on cotton and about 80% on polyester/cotton blends.

In still yet another embodiment, the aqueous treating solution for imparting low formaldehyde and formaldehyde free antimicrobial finishing comprises a heterocyclic amine (e.g., DMDMH, alkylated DMDMH, or a mixture thereof) with DMH. In a preferred embodiment, the foregoing aqueous treating solution optionally comprises a polyol. Admixing DMDMH or MDMH with DMH results in formaldehyde reduction in a range of about 60% on cotton and about 60% on polyester/cotton blends.

Those of skill in the art will readily appreciate that other additives can optionally be incorporated into the aqueous treating solution to impart favorable characteristics to microbiocidal articles. Such additives can include softeners and waterproofing agents that are known to and used by those of skill in the art. Examples of softeners which can be added to the aqueous treating solution include, but are not limited to, MYKON® and SEQUASOFT® both of which are commercially available from Sequa Chemical Inc. (Chester, S.C.). Examples of waterproofing agents which can be added to the aqueous treating solution include, but are not limited to, SEQUAPEL® (Sequa Chemical Inc., Chester, S.C.), SCOTCHGARD® (3 M, St. Paul, Minn.) and other water repellent finishing solutions used by those of skill in the art.

In certain aspects, the microbiocidal articles produced using the present processes possess regenerable and durable properties. For instance, after effective microbiocidal activity is obtained, and subsequently exhausted, the article can be rendered capable of possessing microbiocidal properties again. By retreating the article with a halogenated solution the microbiocidal activity can be regenerated. As such, using the processes of the present invention, microbiocidal properties are imparted onto articles, such as textiles, and these properties are regenerable.

Furthermore, the microbiocidal properties imparted onto articles are durable. The durability of the process and its potential to antimicrobial was demonstrated after laundering. Thus, the functional finishing on the article (e.g., cotton/polyester fabric) is durable, surviving many machine washes without compromising its microbiocidal potential. These finished fabrics can therefore provide optimum protection as well as comfort to the wearers.

EXAMPLES

The following examples are offered to illustrate, but not to limit the claimed invention.

Example 1

This Example illustrates the use of an alkylated heterocyclic amine to reduce free-formaldehyde.

A solution of 18.8 parts of DMDMH and 64 parts of methanol were acidified with hydrochloric acid to a pH value of 2.5–3.5 and then heated for 2 hours at 50° C. The resulting product was a clear liquid with a very slight odor of formaldehyde and this product was used to treat a 100% cotton fabric as follows. A 100 mL aqueous solution containing 17 parts of the product, 2 parts of Catalyst 531 (Sequa Chemical Inc., Chester, S.C.) and 0.1 part of TRITON-X 100 was applied to the fabric by padding at a wet pick-up of 90% based on the weight of the fabric. The treated fabric was dried for 5 minutes at 80° C. and cured for 6 minutes at 160° C. or 1.5 minutes at 200° C. The fabric was tested for formaldehyde content on fabric without washing. The results indicated a 58% reduction of formaldehyde on pure cotton and a 70% reduction on polyester/cotton blends.

Example 2

This Example illustrates the use of a heterocyclic amine and a polyol to reduce free-formaldehyde.

48 grams of DMDMH (0.2553 mole) and 60 grams of diethylene glycol (0.5660 mole) were reacted in 93 grams of water and were subsequently acidified with sulfuric acid to a pH value of 3.0 and heated for 6 hours at 75° C. The resulting product was a clear liquid with a very slight odor of formaldehyde.

The product was then used to treat a 100% cotton fabric as follows. A 100 mL aqueous solution containing 15.88 parts of the product, 2 parts of Catalyst 531 and 0.1 part of TRITON-X 100 was applied to the fabric by padding at a wet pick-up of 90% based on the weight of the fabric. The treated fabric was dried for 5 minutes at 80° C. and cured for 6 minutes at 160° C. or 1.5 minutes at 200° C. The fabric was tested for free-formaldehyde on fabric without washing. The results indicated a 48% reduction of formaldehyde on cotton and a 46% reduction on polyester/cotton blends.

Example 3

This Example illustrates the use of an alkylated heterocyclic amine and a polyol to reduce free-formaldehyde.

A 100 mL of an aqueous finishing solution containing 17 parts of the product of Example 1 and two parts of Catalyst 531, 0.1 parts of TRITON-X and 4.34 parts of diethylene glycol were applied to a fabric under the same conditions as set forth in Example 1. The treated fabric was dried for 5 minutes at 80° C. and cured for 6 minutes at 160° C. or 1.5 minutes at 200° C. The fabric was tested for free-formaldehyde on fabric without washing. The results indicted a 68–82% reduction of formaldehyde on cotton and a 63–73% reduction on polyester/cotton blends.

Example 4

This Example illustrates the use of a heterocyclic amine and a polyol to reduce free-formaldehyde.

A 600 mnL aqueous solution containing 69 parts of a 34.78% DMDMH solution (0.1277 moles) and 30 parts of diethylene glycol (0.2830 moles), 12 parts of Sequa Catalyst 531, and 0.6 parts of TRITON X-100 were applied to a fabric. The treated fabric was dried for 5 minutes at 80° C. and cured for 6 minutes at 160° C. or 1.5 minutes at 200° C. The fabric was tested for free-formaldehyde on fabric. The results indicated a 58–70% reduction of formaldehyde on cotton and a 67–70% reduction on polyester/cotton blends.

Example 5

This Example illustrates the use of a heterocyclic amine, a polyol and softener to reduce free-formaldehyde.

A 100 mL aqueous solution containing 3.85 Parts of DMDMH (0.02 moles) and 6.51 parts of diethylene glycol (0.06 moles), 2 parts of catalyst 531, 0.1 parts of TRITON-X, with or without 3% fabric softener (MYKON available from Sequa Chemical Inc. Chester, S.C.) was applied to a fabric. The treated fabric was dried for 5 minutes at 80° C. and cured one sample for 1.5 minutes at 200° C. The fabric was tested for free-formaldehyde on fabric, with a 78–80% reduction on cotton and a 67–79% reduction on polyester/cotton.

Example 6

This Example illustrates the use of a heterocyclic amine and polyol to reduce free-formaldehyde.

A 100 mL aqueous finishing solution containing 16.12 parts of the product of Example 2 and 4.35 parts of diethylene glycol, 2 parts of catalyst 531, 0.1 parts of TRITON-X was applied to a fabric. The treated fabric was dried for 5 minutes at 80° C. and cured for 1.5 minutes at 200° C. The fabric was tested for free-formaldehyde on fabric. The results indicated a 80% reduction of formaldehyde on cotton and a 79% reduction on polyester/cotton blends.

Example 7

This Example illustrates the use of a combination of heterocyclic amines, a polyol and softener to reduce free-formaldehyde.

A 100 mL aqueous finishing solution containing 2 parts of DMDMH (0.0106 mole) and 1.89 parts of DMDHEU (0.0106 mole), 2 parts of Catalyst 531, 0.1 parts of TRITON-X, with or without 3 parts of a fabric softener was applied to a fabric. The treated fabric was dried for 5 minutes at 80° C. and cured for 1.5 minutes at 200° C. The fabric was tested for free-formaldehyde on fabric. The results indicated a 77% reduction of formaldehyde on cotton and an 82% reduction on polyester/cotton blends. The fabric after bleaching in a chlorine solution exhibited durable biocidal effects.

Example 8

This Example illustrates the use of a combination of heterocyclic amines and softener to reduce free-formaldehyde.

A 100 mL aqueous finishing solution containing 3.85 parts of DMDMH (0.02 moles) and 3.2 parts of 5,5-dimethylhydantoin (0.025 moles), 2 parts of Catalyst 531, 0.1 parts of TRITON-X with or without 3% fabric softener (MYKON) was applied to a fabric. The treated fabric was dried for 5 minutes at 80° C. and cured one sample for 1.5 minutes at 200° C. The fabric was tested for free-formaldehyde on fabric. The results indicated a 59% reduction of formaldehyde on cotton and a 63% reduction on polyester/cotton blends.

Example 9

This Example illustrates a control process using a heterocyclic amine only.

The fabric was treated with DMDMH instead of the product of this invention under the same conditions. The fabric was tested for free-formaldehyde on fabric without washing, with 1191–1333 ppm on cotton and 950–1141 ppm on polyester/cotton.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A process for preparing a microbiocidal article with a reduction in free-formaldehyde release, said process comprising:
   (a) immersing said article in an aqueous treating solution which comprises a heterocyclic amine and a polyol; and
   (b) treating said article with a halogenated solution to produce a heterocyclic N-halamine, thereby rendering said article microbiocidal with a reduction in free-formaldehyde release.

2. The process according to claim 1, wherein said aqueous treating solution further comprises a catalyst and a wetting agent.

3. The process according to claim 1, wherein said heterocyclic amine is alkylated or partially alkylated.

4. The process according to claim 1, wherein said polyol is a member selected from the group consisting of ethylene glycol, propylene glycol, diethylene glycol, 1,2-propylene glycol, 1,3-propylene glycol, 1,2-butylene glycol, 1,3-butylene glycol, 1,4-butylene glycol, polyethylene glycols having the formula $HO(CH_2CH_2)_nH$ wherein n is about 1 to about 50, glycerin and combinations thereof.

5. The process according to claim 4, wherein said polyol is ethylene glycol.

6. The process according to claim 4, wherein said polyol is diethylene glycol.

7. The process according to claim 1, wherein said heterocyclic amine and said polyol are present in said treating solution in a heterocyclic amine:polyol ratio between about 0.2:1.0 to about 1.0:6.0 mole/mole.

8. The process according to claim 7, wherein said heterocyclic amine:polyol ratio is about 0.5:1.0 to about 1.0:3.0 mole/mole.

9. The process according to claim 1, wherein said heterocyclic amine is a member selected from the group consisting of monomethylol-5,5-dimethylhydantoin (MDMH), 1,3-dimethylol-5,5-dimethylhydantoin (DMDMH), 5,5-dimethylhydantoin (DMH); monoalkylolated and dialkylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid and 5,5-dimethylhydantoin (DMH); and monoalkylated and dialkylated derivatives of monoalkylolated and dialkylolated derivatives of 2,2,5,5-tetramethyl-1,3-imidazolidin-4-one 6,6-dimethyl-1,3,5-triazine-2,4-dione, 4,4,5,5-tetramethyl-1,3-imidazolidin-2-one, cyanuric acid, and 5,5-dimethylhydantoin, an alkylated derivative thereof and mixtures thereof.

10. The process according to claim 9, wherein said heterocyclic amine is 1,3-dimethylol-5,5-dimethylhydantoin (DMDMH) or an alkylated derivative thereof.

11. The process according to claim 9, wherein said heterocyclic amine is monomethylol-5,5-dimethylhydantoin (MDMH) or an alkylated derivative thereof.

12. The process according to claim 1, further comprising dimethyloldihydroxyethylene urea (DMDHEU) or an alkylated derivative thereof.

13. The process according to claim 10, further comprising dimethyloldihydroxyethylene urea (DMDHEU) or an alkylated derivative thereof.

14. The process according to claim 11, further comprising dimethyloldihydroxyethylene urea (DMDHEU) or an alkylated derivative thereof.

15. The process according to claim 10, further comprising 5,5-dimethylhydantoin (DMH).

16. The process according to claim 11, further comprising 5,5-dimethylhydantoin (DMH).

17. The process of claim 1, further comprising removing excess aqueous treating solution from said article before treating said article with a halogenated aqueous solution.

18. The process of claim 17, further comprising drying said article after removing excess aqueous treating solution to produce a dried article.

19. The process of claim 18, further comprising curing said dried article to produce a cured article.

20. The process of claim 19, further comprising washing said cured article to remove excess reagents.

21. The process of claim 20, further comprising drying said washed article to remove water.

22. The process of claim 1, wherein said article is a textile.

23. The process of claim 22, wherein said textile is a member selected from the group consisting of cellulosic fabric, cellulosic yarn, and cellulosic fiber.

24. The process of claim 22, wherein said textile is cotton fabric.

25. The process of claim 22, wherein said textile is cotton fabric/polyester blend.

26. The process of claim 1, wherein said article is a polymer.

27. The process of claim 26, wherein said polymer is a member selected from the group consisting of cellulose and a synthetic polymer.

28. The process of claim 1, wherein said halogenated aqueous solution comprises sodium hypochlorite.

29. The process of claim 2, wherein said catalyst is a member selected from the group consisting of $MgCl_2$, $Mg(NO_3)_2$, $Zn(NO_3)_2$ and $NH_4NO_3$.

30. A process for preparing a microbiocidal article with a reduction in free-formaldehyde release, said process comprising:

(a) immersing said article in an aqueous treating solution which comprises an alkylated hydantoin derivative; and (b) treating said article with a halogenated solution to produce an N-halo-hydantion derivative, thereby rendering said article microbiocidal with a reduction in free-formaldehyde release.

31. The process according to claim 30, wherein said alkylated heterocyclic amine is alkylated or partially alkylated 1,3-dimethylol-5,5-dimethylhydantoin (DMDMH).

32. The process according to claim 30, wherein said alkylated heterocyclic amine is alkylated or partially alkylated monomethylol-5,5-dimethylhydantoin (MDMH).

33. The process according to claim 30, wherein said aqueous treating solution further comprises a catalyst and a wetting agent.

* * * * *